United States Patent
Tamura et al.

(10) Patent No.: US 8,911,955 B2
(45) Date of Patent: Dec. 16, 2014

(54) VIRUS DETECTION DEVICE AND VIRUS DETECTION METHOD

(71) Applicant: Tokyo Electron Limited, Tokyo (JP)

(72) Inventors: Akitake Tamura, Nirasaki (JP); Kaoru Fujihara, Nirasaki (JP); Misako Saito, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 64 days.

(21) Appl. No.: 13/871,316

(22) Filed: Apr. 26, 2013

(65) Prior Publication Data

US 2013/0244226 A1  Sep. 19, 2013

Related U.S. Application Data

(63) Continuation of application No. PCT/JP2011/005767, filed on Oct. 14, 2011.

(30) Foreign Application Priority Data

Oct. 29, 2010  (JP) ................................ 2010-244474

(51) Int. Cl.
  *G01N 33/569* (2006.01)
  *G01N 15/06* (2006.01)
  *G01N 15/00* (2006.01)

(52) U.S. Cl.
  CPC .......... *G01N 33/56983* (2013.01); *G01N 15/06* (2013.01); *G01N 2333/09* (2013.01); *G01N 2333/11* (2013.01); *G01N 2015/0065* (2013.01); *G01N 2015/0046* (2013.01); *G01N 2015/0693* (2013.01); *G01N 2015/0038* (2013.01)
  USPC .............. 435/7.1; 435/5; 435/287.2

(58) Field of Classification Search
  CPC ............ G01N 15/06; G01N 33/56893; G01N 2333/09; G01N 2333/11; G01N 2015/0038; G01N 2015/0046; G01N 2015/0065; G01N 2015/0693
  See application file for complete search history.

(56) References Cited

U.S. PATENT DOCUMENTS

2002/0006670 A1  1/2002  Wu et al.

FOREIGN PATENT DOCUMENTS

| CN | 100344972 C | 10/2007 |
|----|----|----|
| JP | 2001-518624 A | 10/2001 |
| JP | 2008-256701 A | 10/2008 |

OTHER PUBLICATIONS

Makoto, et al., "Developed Airport Quarantine, a Bioterrorism Measures for Sensitive Pathogen Detection Method", National Institute of New Energy and Industrial Technology Development Organization, Nagahama Institute of Bio-Science, Oct. 8, 2008, located online on Jul. 6, 2010, can be located at http://www.nedo.go/jp/informations/press201008_1/201008_1.html.

(Continued)

*Primary Examiner* — Louise Humphrey
(74) *Attorney, Agent, or Firm* — Pearne & Gordon LLP

(57) ABSTRACT

A virus detection device includes a diffusion unit configured to diffuse a virus in a gas as an inspection target into an aqueous solution containing a fluorescent antibody specifically adsorptive to the virus by bringing the gas into contact with the aqueous solution and configured to adsorb the fluorescent antibody to the virus in the gas; an atomization unit configured to atomize the aqueous solution and generate a mist group of the aqueous solution in which the gas is diffused; a fluorescence measuring unit configured to measure a fluorescence intensity of the mist group; and an air current generator configured to form an air current flowing toward the fluorescence measuring unit from the atomization unit.

5 Claims, 6 Drawing Sheets

(56) References Cited

OTHER PUBLICATIONS

International Search Report for PCT/JP2011/005767 dated Nov. 8, 2011.

McElhoney, et al., "CHED 241—Gentle Capture of an Airborne Virus for Online Detection with Flow Cytometry", Aug. 20, 2007.

Lee, et al., "Real-time detection of Airborne Viruses on a Mass-sensitive Device", Jul. 8, 2008, Applied Physics Letters, vol. 93.

VIRUS DETECTION DEVICE AND VIRUS DETECTION METHOD

CROSS-REFERENCE TO RELATED APPLICATION

This Application is a Continuation of International Application No. PCT/JP2011/005767 filed on Oct. 14, 2011, which claims the benefit of Japanese Patent Application No. 2010-244474 filed on Oct. 29, 2010. The entire disclosure of the prior application is incorporated herein by reference in its entirety.

FIELD OF THE INVENTION

The present disclosure relates to a technique for detecting a virus.

BACKGROUND OF THE INVENTION

Recently, the wide spread of infectious diseases such as influenza and the expansion of a range of infection are considered as serious problems. In order to promptly solve the problems for public heath, there has been a demand for a highly precise and simple method for virus analysis. Currently, in quarantine inspection, a cleaning liquid after cleaning one's nasal cavity is analyzed. However, this inspection method has problems in sensitivity and time period for diagnosis. Further, in order to take measures against pandemic and bio terrors, viruses in the atmosphere need to be inspected constantly. In a manual inspection method conducted by a human being, such as inspecting the cleaning liquid from the nasal cavity, it is difficult to expect the automation of the virus analysis. As for the analysis of, e.g., an influenza virus in the atmosphere, there is a cultivation method for observing and analyzing colonies formed after culturing the virus adhered to a culture medium. However, this cultivation method has drawbacks in that it takes several days for the cultivation and it is difficult to automate the cultivation method. Thus, this cultivation method may not be useful when prompt analysis is required in such cases as dealing with a novel influenza, a foot-and-mouth disease virus, and the like. Additionally, there may be employed a method for detecting a virus in the atmosphere by trapping the virus in a liquid. In this method, however, due to low sensitivity of analysis in the liquid, the virus may not be precisely detected.

Under these circumstances, Non-Patent Document 1 describes a method for detecting a virus with high sensitivity in a short time period by selectively adsorbing a fluorescent antibody in a certain virus and then measuring fluorescence intensity. In the method of Non-Patent Document 1, however, a mucous membrane or saliva is analyzed as a sample and the analysis is not conducted automatically on a real time basis. Further, in the above method of Non-Patent Document 1, presence or absence of a virus is determined by detecting a variation difference in the fluorescence intensity, not by an absolute value of the fluorescence intensity.

Non-Patent Document 1: Hasegawa Makoto, "Development of High Sensitivity Pathogenic Organism Detection Method for Airport Quarantine and against Bio Terror," [online], Oct. 8, 2008, New Energy and Industrial Technology Development Organization, [Searched on Jul. 6, 2010], Internet <URL: http://www.nedo.go.jp/informations/press201008_1/201008_1.html>

BRIEF SUMMARY OF THE INVENTION

In view of the foregoing problems, the present disclosure provides a technique for precisely detecting a virus in the atmosphere on a real time basis.

In accordance with one aspect of the illustrative embodiment, there is provided a virus detection device including a diffusion unit configured to diffuse a virus in a gas as an inspection target into an aqueous solution containing a fluorescent antibody specifically adsorptive to the virus by bringing the gas into contact with the aqueous solution and configured to adsorb the fluorescent antibody to the virus in the gas; an atomization unit configured to atomize the aqueous solution and generate a mist group of the aqueous solution in which the gas is diffused; a fluorescence measuring unit configured to measure a fluorescence intensity of the mist group; and an air current generator configured to form an air current flowing toward the fluorescence measuring unit from the atomization unit.

In accordance with another aspect of the illustrative embodiment, there is provided a virus detection method including diffusing a virus in a gas as an inspection target into an aqueous solution containing a fluorescent antibody specifically adsorbed to the virus by bringing the gas into contact with the aqueous solution, and adsorbing the fluorescent antibody to the virus in the gas; atomizing the aqueous solution and generating a mist group of the aqueous solution in which the gas is diffused; and measuring a fluorescence intensity of the mist group.

In accordance with the illustrative embodiment, the virus in the gas as an inspection target is diffused into the aqueous solution containing the fluorescent antibody specifically adsorbed to a certain virus. Then, mist of the chemical liquid is generated and fluorescence intensity of the mist is measured. With this method, presence or absence of the certain virus in the gas can be detected automatically on a real time basis.

BRIEF DESCRIPTION OF THE DRAWINGS

Non-limiting and non-exhaustive embodiments will be described in conjunction with the accompanying drawings. Understanding that these drawings depict only several embodiments in accordance with the disclosure and are, therefore, not to be intended to limit its scope, the disclosure will be described with specificity and detail through use of the accompanying drawings, in which.

DETAILED DESCRIPTION OF THE INVENTION

Figure 1:
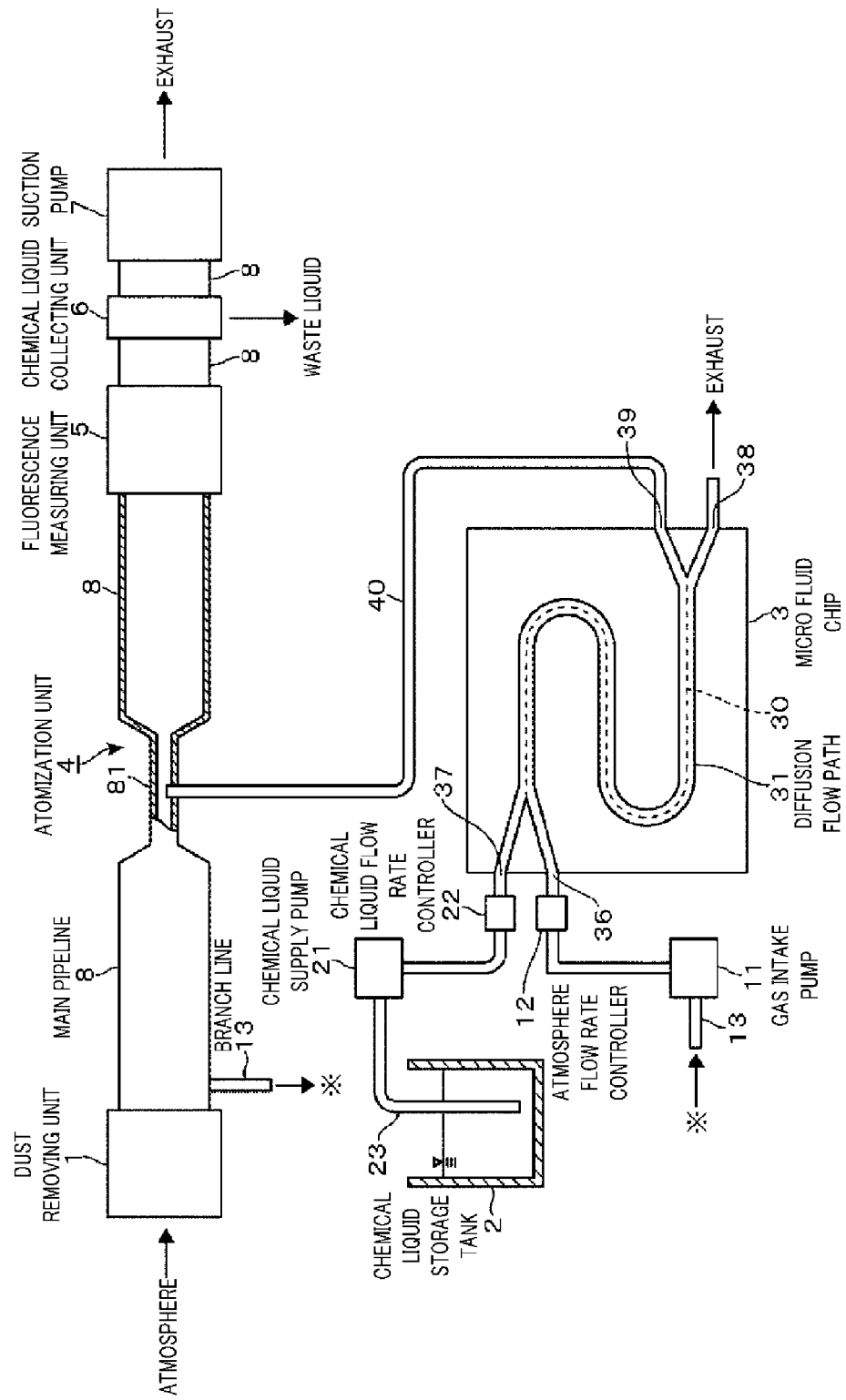
FIG. 1 is a schematic view illustrating a configuration of a virus detection device in accordance with an illustrative embodiment.

Configuration of a virus detection device in accordance with an illustrative embodiment will be explained with reference to FIGS. 1 to 3. As illustrated in FIG. 1, the virus detection device includes a main pipeline 8 configured as a guide passage of an air current. A dust removing unit 1 is provided at an upstream end of the main pipeline 8, and a suction pump 7 serving as an air current generator is provided at a downstream end of the main pipeline 8. The dust removing unit 1 is configured to allow a virus V to pass therethrough and required to have an enough air current resistance to form a fast air current capable of generating atomization in the main pipeline 8. To this end, the dust removing unit 1 is configured to capture relatively large-sized particles. Further, in the main pipeline 8, there is provided an atomization unit 4 configured to generate mist of a chemical liquid supplied from a micro fluid chip 3 serving as a diffusion unit to be described later.

Figure 2:
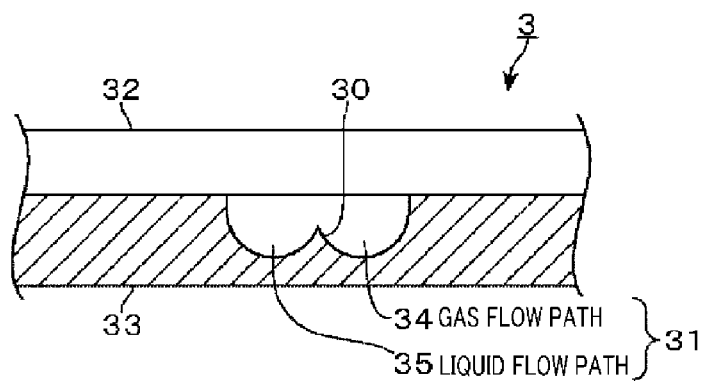
FIG. 2 is a longitudinal side view illustrating a part of a micro fluid chip used in the illustrative embodiment.
Figure 3:
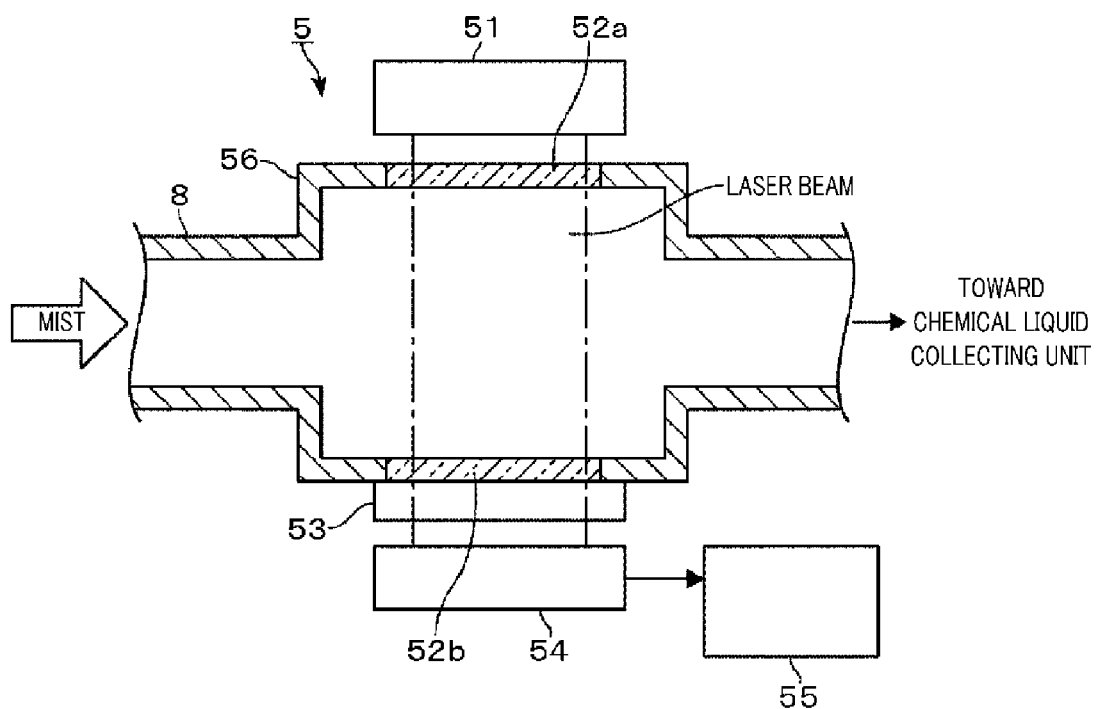
FIG. 3 is a longitudinal side view illustrating a fluorescence measuring unit used in the illustrative embodiment.

As illustrated in FIG. 2, the micro fluid chip 3 includes a cover 32 and a plate-shaped body 33. A groove 31 is formed on a top surface of the plate-shaped body 33. The groove 31 is covered by the cover 32 to serve as a diffusion flow path 31. As illustrated in FIG. 2, the diffusion flow path 31 has a cross section in the form of two semicircles, which are arranged next to each other horizontally and partially overlapped with each other. A protrusion 30 is formed at a middle part of the flow path. The diffusion flow path 31 is partitioned by the protrusion 30 into a gas flow path 34 and a liquid flow path 35. As for the dimension of the diffusion flow path 31, a width (W) of the diffusion flow path 31 is set to be equal to or less than, e.g., about 1 mm; a depth (H) thereof is set to be, e.g., about 0.5 mm; and a height of a gap between the protrusion 30 and the cover 32 is set to be, e.g., about 0.2 mm. As illustrated in FIG. 1, in order to obtain sufficient contact time between the atmosphere and the chemical liquid and a contact area therebetween, the diffusion flow path 31 is formed to meander. Both ends of the diffusion flow path 31 are branched into two lines at branch points and reach end portions of the micro fluid chip 3 in this state. One end (upstream end) of the diffusion flow path 31 corresponds to an atmosphere inlet port 36 and a chemical liquid inlet port 37. The other end (downstream end) of the diffusion flow path 31 corresponds to an exhaust port 38 and a chemical liquid outlet port 39.

As illustrated in FIG. 1, a branch line 13 branched from the main pipeline 8 between the dust removing unit 1 and the atomization unit 4 is airtightly connected to the atmosphere inlet port 36 of the micro fluid chip 3. A gas intake pump 11 as a gas introduction unit and an atmosphere flow rate controller 12 are provided at the branch line 13 in this order from the upstream side thereof. Connected to the chemical liquid inlet port 37 is a pipeline 23 led from a chemical liquid storage tank 2 that stores therein a chemical liquid, which is an aqueous solution containing a fluorescent antibody F. Further, a chemical liquid supply pump 21 as a liquid introduction unit and a chemical liquid flow rate controller 22 are provided at the pipeline 23 in this order from the chemical liquid storage tank 2. The exhaust port 38 of the micro fluid chip 3 is connected to an outside of the virus detection device. The atmosphere introduced into the micro fluid chip 3 is exhausted through the exhaust port 38. The chemical liquid outlet port 39 of the micro fluid chip 3 is connected to the aforementioned atomization unit 4 via a chemical liquid supply line 40, which is a guide passage.

The atomization unit 4 includes a part 81 of the main pipeline 8 of which diameter is sharply narrowed; and the chemical liquid supply line 40 inserted into the part 81 of the main pipeline 8. The chemical liquid supply line 40 serves as a guide passage through which the chemical liquid from the micro fluid chip 3 is flown.

A fluorescence measuring unit 5 is provided at a downstream side of the atomization unit 4. As illustrated in FIG. 3, the fluorescence measuring unit 5 includes a case 56 of, e.g., a quadrangle shape. The case 56 forms a space through which an air current including mist M flows. Light transmitting windows 52a and 52b made of, e.g., quartz are arranged at the case 56, for example, at top and bottom (or right and left) surfaces thereof such that the light transmitting windows 52a and 52b face each other. Disposed outside one light transmitting window 52a is a light emitting unit 51 that irradiates a laser beam having a wavelength deviated from a wavelength of fluorescence emitted from the fluorescent antibody F into the case 56. Further, disposed outside the other light transmitting window 52b is an optical filter 53 that blocks light having a wavelength deviated from the wavelength of fluorescence emitted from the fluorescent body F. Disposed at a further outer position with respect to the light transmitting window 52b is a light receiving unit 54 that receives the fluorescence of the fluorescent antibody F to convert the fluorescence into an electrical signal. The light receiving unit 54 outputs a signal level, e.g., an electric current, corresponding to the intensity of the light received from the optical filter 53 to a received light output measuring unit 55. For example, the received light output measuring unit 55 converts the electric current into a voltage and compares the voltage signal Ia with a preset threshold value Is. If it is determined that the voltage signal Ia is larger than the threshold value Is, the received light output measuring unit 55 may output an alarm indicating virus detection or display the virus detection on a non-illustrated display unit.

Figure 4:
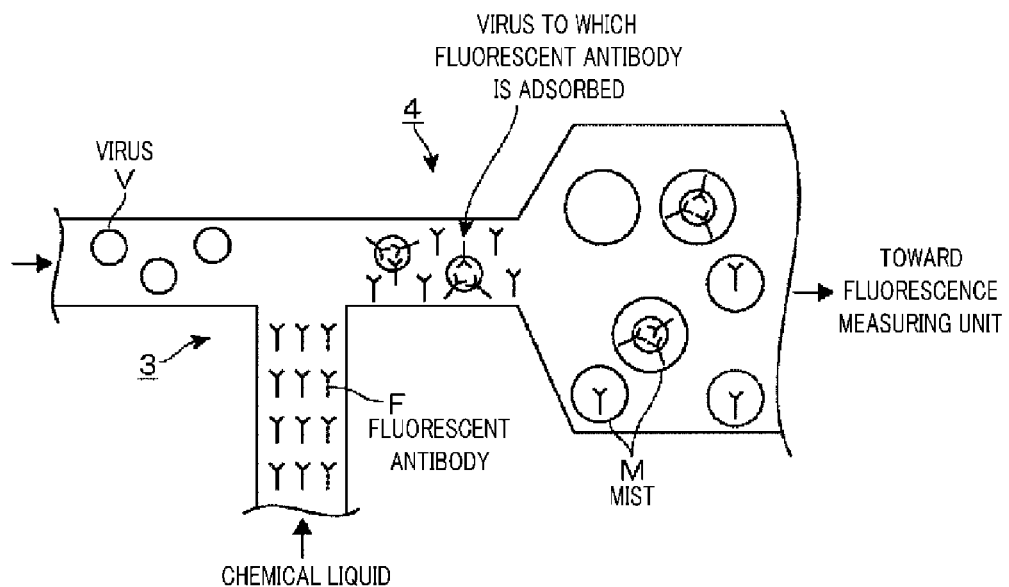
FIG. 4 is a conceptual view for describing a virus diffusion in a chemical liquid, adsorption of a fluorescent antibody and atomization of the chemical liquid in a diffusion unit.
Figure 5:
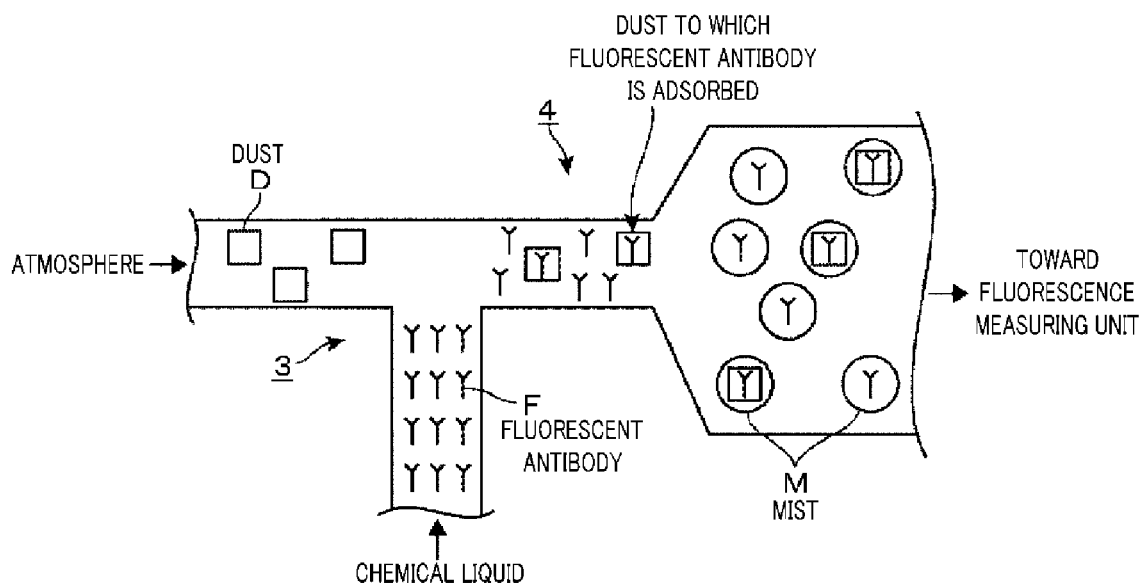
FIG. 5 is a conceptual view for describing diffusion of dust in the atmosphere in a chemical liquid, adsorption of a fluorescent antibody and atomization of the chemical liquid in the diffusion unit.

Since the voltage signal Ia is a signal corresponding to the intensity of the received light, the threshold value Is may be determined as follows. That is, the threshold Is is set to a value between a fluorescence intensity when no virus V exists in the atmosphere; and a fluorescence intensity when the mist M, in which the fluorescent antibody F is adsorbed a virus V in the atmosphere, passes through the case 56. The fluorescence intensity when no virus V exists in the atmosphere corresponds to an intensity of fluorescence from a fluorescent antibody F adhered to a dust D contained in the atmosphere passing through the case 56 or a fluorescent antibody F contained in the mist M of the chemical liquid. The fluorescent antibody F is specifically adsorbed to the virus V. Thus, roughly speaking, when the virus V exists, a density of the fluorescent antibody F becomes higher than a density of the fluorescent antibody when no virus V exists, as illustrated in FIGS. 4 and 5 to be described later. Accordingly, there is generated a difference in fluorescence intensity between the two cases when the virus V exists and when no virus V exists.

At a downstream side of the fluorescence measuring unit 5, there is provided a chemical liquid collecting unit 6 formed of, for example, a mesh member for capturing mist M of the chemical liquid. Further, the suction pump 7 is provided at a downstream side of the chemical liquid collecting unit 6. A separated gas is exhausted to an outside of the device via, e.g., a non-illustrated filter for adsorbing and removing a virus.

Now, an operation of the virus detection device in accordance with the present illustrative embodiment will be explained. First, the atmosphere (exterior air) is introduced into the main pipeline 8 via the dust removing unit 1 by the suction pump 7. There is generated an air current that flows through the atomization unit 4, the fluorescence measuring unit 5 and the chemical liquid collecting unit 6 in this order. The air current is exhausted via the suction pump 7 and the non-illustrated filter. Here, the dust removing unit 1 removes a large-sized dust in the atmosphere that may block the diffusion flow path 31 of the micro fluid chip 3 or interrupt fluorescence detection in the fluorescence measuring unit 5. A part of the atmosphere introduced into the main pipeline 8 is flown into the atmosphere inlet port 36 of the micro fluid chip 3 by the gas intake pump 11. The chemical liquid containing the fluorescent antibody F is flown from the chemical liquid storage tank 2 into the chemical liquid inlet port 37 of the micro fluid chip 3 by the chemical liquid supply pump 21.

The atmosphere flow rate controller 12 and the chemical liquid flow rate controller 22 set a flow rate of the atmosphere flown into the atmosphere inlet port 36 and a flow rate of the chemical liquid flown into the chemical liquid inlet port 37, respectively, to appropriate values obtained in advance through experiments. Accordingly, the atmosphere and the chemical liquid introduced into the micro fluid chip 3 flow side by side while forming an interface on the protrusion 30 of the diffusion flow path 31. That is, the atmosphere flows through the gas flow path 34 in the diffusion flow path 31 toward the exhaust port 38. The chemical liquid flows through the liquid flow path 35 in the diffusion flow path 31 toward the chemical liquid outlet port 39. When the atmosphere and the chemical liquid flow within the micro fluid chip 3 in this way, a virus V in the atmosphere is diffused into the chemical liquid via the interface. The fluorescent antibody F in the chemical liquid is specifically adsorbed to the virus V. The atmosphere and the chemical liquid are separated from each other at a branch point near the outlet of the diffusion flow path 31. Then, the atmosphere is exhausted to the outside of the device via the exhaust port 38, and the chemical liquid is flown into the atomization unit 4 through the chemical liquid outlet port 39 and the chemical liquid supply line 40 serving as the guide passage.

In the atomization unit 4, the chemical liquid sent from the micro fluid chip 3 through the chemical liquid supply line 40 is atomized by the air current. Here, the air current has been already speeded up as the main pipeline is sharply narrowed. That is, the chemical liquid is attracted from the outlet of the chemical liquid supply line 40 toward the high-speed air current to be groups of mist M. Then, the groups of mist M of the chemical liquid ride on the air current and are guided to the fluorescence measuring unit 5 through the guide passage of the main pipeline 8 at the downstream side of the atomization unit 4.

In the fluorescence measuring unit 5, e.g., an ultraviolet laser beam is irradiated from the light emitting unit 51 toward the case 56 through which the atomized chemical liquid flows. At this time, the fluorescent antibody F in the atomized chemical liquid fluoresces by the ultraviolet laser beam. The ultraviolet laser beam is blocked by the optical filter 53, while light having a wavelength of fluorescence is detected by the light receiving unit 54. The detected light intensity at this time is in proportion to a volumetric density of the fluorescent antibody F in the mist M of the chemical liquid. If no virus V exists in the mist M of the chemical liquid, as illustrated in FIG. 5, a fine dust D in the atmosphere may be introduced into the mist M. Thus, even though the florescent antibody F adheres to the dust D, the density of the fluorescent antibody F may be much lower than the density of the fluorescent antibody F adsorbed to the virus V. Accordingly, the light intensity detected by the light receiving unit 54 may be smaller than the preset threshold value Is. Meanwhile, if a virus V exists in the mist M of the chemical liquid, the fluorescence intensity detected by the light receiving unit 54 may become higher than the threshold value Is. In this case, the received light output measuring unit 55 notifies the detection of the virus V.

The mist M having passed through the fluorescence measuring unit 5 is gas-liquid separated in the chemical liquid collecting unit 6. The separated chemical liquid is collected, whereas the separated gas is exhausted to the outside of the device by the suction pump 7 provided at the downstream of the chemical liquid collecting unit 6.

In accordance with the above-described illustrative embodiment, the virus V in the atmosphere as a target of inspection is diffused in the chemical liquid (aqueous solution) containing the fluorescent antibody F that is specifically adsorbed to the certain virus V. The mist M of the chemical liquid is generated and the fluorescence intensity of the mist M is measured. When the virus V exists, the fluorescent antibody F is specifically adsorbed to the virus V so that the number of the fluorescent antibodies F in the mist M is increased. Accordingly, the intensity of the fluorescence emitted from the mist M when the virus V exists becomes greater than the intensity of the fluorescence emitted from the mist M when no virus V exists. The laser beam is blocked by the optical filter 53, and the intensity of the fluorescence that has transmitted the optical filter 53 is measured and compared with the fluorescence intensity (threshold value) corresponding to the intensity of the fluorescence emitted from the mist M when no virus V exists. Accordingly, the virus V contained in the atmosphere can be detected with high precision on a real time basis. In addition, since the virus detection can be automatically performed, the virus V can be monitored constantly. Hence, when used in an airport or the like, the virus detection device in accordance with the present illustrative embodiment will be very effective because a virus V can be detected promptly and an immediate countermeasure thereto can be taken.

In the above-described illustrative embodiment, the atmosphere forming the air current in the main pipeline 8 and the atmosphere in contact with the chemical liquid in the micro fluid chip 3 are supplied from an identical system after passing through the dust removing unit 1. However, besides the dust removing unit 1 in the main pipeline 8, it may be possible to provide an additional dust removing unit and supply the atmosphere to the micro fluid chip 3 through a separate line from the main pipeline 8.

Figure 6:
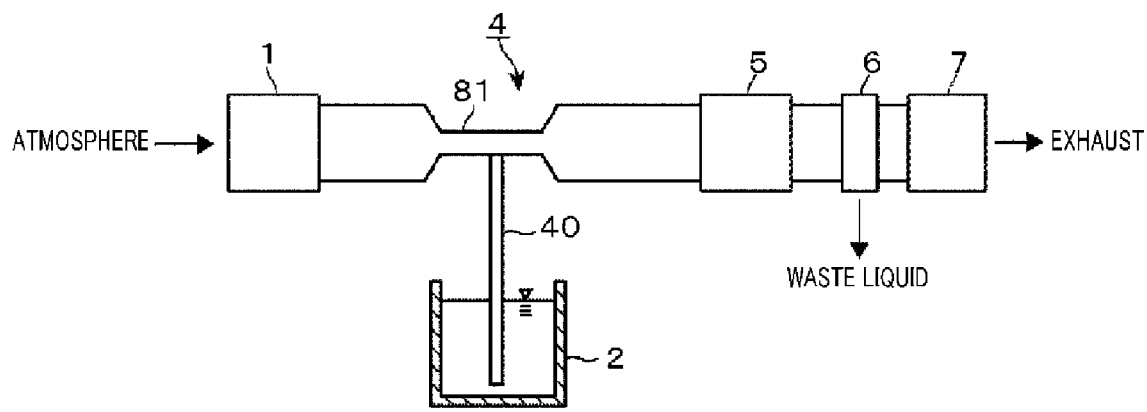
FIG. 6 is a schematic view illustrating a virus detection device in accordance with a second illustrative embodiment.

In the illustrative embodiment of FIG. 1, the micro fluid chip 3 is provided. However, as illustrated in FIG. 6, without providing the micro fluid chip 3, the atomization unit 4 may be provided by submerging one end of the chemical liquid supply line 40 in the chemical liquid storage tank 2 and inserting the other end of the chemical liquid supply line 40 into the narrow part 81 of the main pipeline 8, as in the above-described illustrative embodiment. In this case, a negative pressure is generated at the other end of the chemical liquid supply line 40 due to the air current formed in the main pipeline 8 by the suction pump 7. Accordingly, the chemical liquid in the chemical liquid storage tank 2 is attracted into the main pipeline 8 via the chemical liquid supply line 40 to be atomized (i.e., mist of the chemical liquid is generated). When the virus V in the atmosphere passes through the atomization unit 4, the virus V is introduced into the mist of the chemical liquid generated at the other end of the chemical liquid supply line 40. Accordingly, since the virus V is diffused into the chemical liquid through the atomization unit 4, the atomization unit 4 also functions as the diffusion unit in accordance with this illustrative embodiment. Further, in this illustrative embodiment, the same effect as achieved in the above-described illustrative embodiment may also be obtained.

Figure 7:
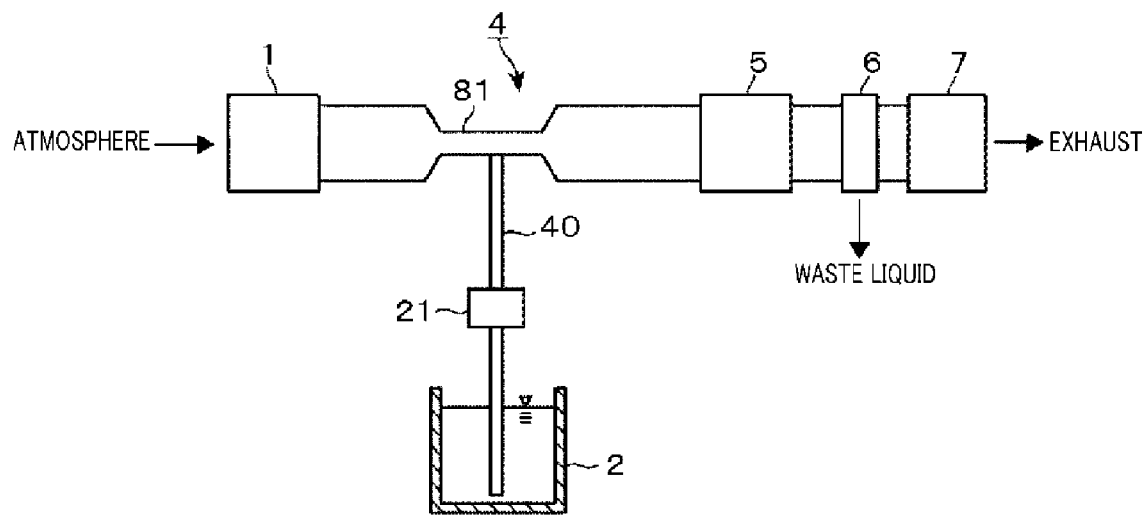
FIG. 7 is a schematic view illustrating a virus detection device in accordance with a third illustrative embodiment.

In the illustrative embodiment where the atomization unit 4 also functions as the diffusion unit, the chemical liquid supply pump 21 may be provided on the way of the chemical liquid supply line 40, as illustrated in FIG. 7. In this case, the chemical liquid in the chemical liquid storage tank 2 may be supplied into the atomization unit 4 through a liquid supplying operation of the chemical liquid supply pump 21.

Figure 8:
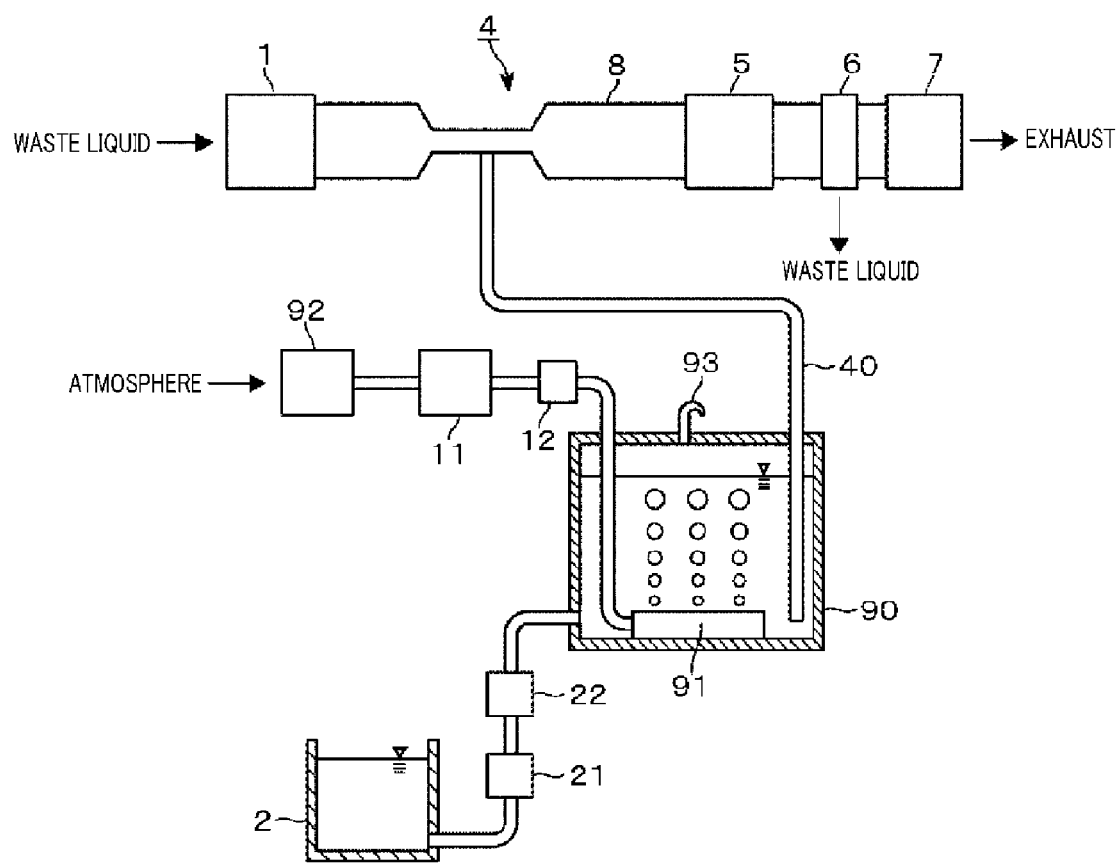
FIG. 8 is a schematic view illustrating a virus detection device in accordance with a fourth illustrative embodiment.

In the illustrative embodiment of FIG. 1, the micro fluid chip 3 is used as the diffusion unit. However, as shown in FIG. 8, an aeration tank 90 may be used as the diffusion unit. In this configuration, the atmosphere may be brought into contact with a chemical liquid in the aeration tank 90 by an air diffusion device 91 so that a virus V in the atmosphere is diffused into the chemical liquid. In FIG. 8, a reference numeral 93 refers to a ventilation port. In this configuration, one end of a chemical liquid supply line 40 may be submerged in the aeration tank 90, and the chemical liquid may be attracted from the other end of the chemical liquid supply line 40 by an air current generated by the suction pump 7, so that the chemical liquid may be atomized. Here, it may be also possible to provide a chemical liquid flow rate controller on the way of the chemical liquid supply line 40, as depicted in FIG. 7.

Figure 9:
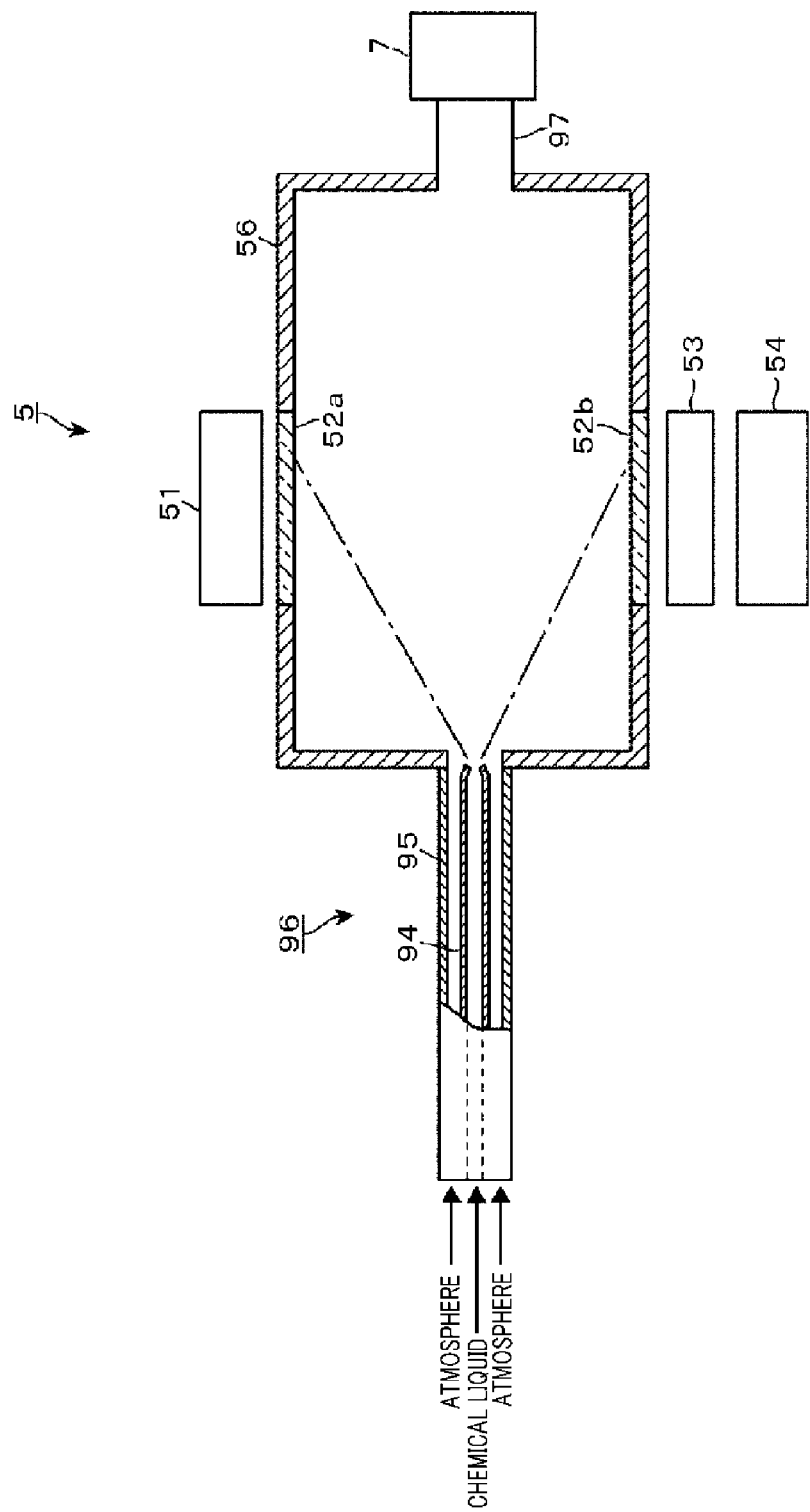
FIG. 9 is a schematic view illustrating an atomization unit and a fluorescence measuring unit of a virus detection device in accordance with a fifth illustrative embodiment.

In accordance with another illustrative embodiment, as shown in FIG. 9, a virus detection device may include a dual pipeline 96 having an inner pipeline 94 and an outer pipeline 95. An opening at a leading end of the inner pipeline 94 may be narrowed, and a leading end of the dual pipeline 96 may be connected to the case 56 of the fluorescence measuring unit 5. A suction pipeline 97 may be connected to a surface of the case 56 facing the leading end of the dual pipeline 96. In this configuration, a chemical liquid may be supplied into the inner pipeline 94 of the dual pipeline 96, and the atmosphere may flow through the outer pipeline 95. The chemical liquid may be flown into the inner pipeline 94 by a non-illustrated chemical liquid flow rate controller. By driving the suction pump 7, the atmosphere may be attracted into the outer pipeline 95. The chemical liquid from the inner pipeline 94 may be atomized into mist groups by an air current of the atmosphere. The mist groups may be dispersed into the case 56 and pass through a light transmitting region in which a laser beam is emitted from the light emitting unit 51. In this embodiment, the leading end of the dual pipeline 96 functions as the diffusion unit and the atomization unit.

In the above-described embodiments, the atmosphere may be exterior air or may be expiration of a human being. In the latter case, one end of a pipeline for introducing the atmosphere may be expanded to have a bugle shape. By blowing from the bugle-shaped part of the pipeline, the expiration of the human being may be introduced into the pipeline.

What is claimed is:

1. A virus detection device comprising:
    a diffusion unit configured to diffuse a gas into an aqueous solution containing a fluorescent antibody specific for a virus, by bringing the gas into contact with the aqueous solution and letting the fluorescent antibody bind the virus in the gas;
    an atomization unit configured to atomize the aqueous solution and generate a mist of the aqueous solution in which the gas is diffused;
    a fluorescence measuring unit configured to measure a fluorescence intensity of the mist with and without viruses; and
    an air current generator configured to form an air current flowing toward the fluorescence measuring unit from the atomization unit.

2. The virus detection device of claim 1, wherein the diffusion unit comprises:
    a diffusion flow path including a liquid flow path through which the aqueous solution flows;
    a gas flow path, formed in parallel to the liquid flow path, through which the gas flows while bringing the gas into contact with the aqueous solution flowing through the liquid flow path; and
    a branch part that is formed at an outlet of the diffusion flow path and configured to discharge the gas and the aqueous solution after separating the gas and the aqueous solution,
    wherein the virus detection device further comprises:
    a gas introduction unit and a liquid introduction unit configured to introduce the gas and the aqueous solution into the diffusion flow path, respectively; and
    a guide passage configured to guide the aqueous solution separated at the branch part into the atomization unit.

3. The virus detection device of claim 1, wherein the atomization unit contains the diffusion unit.

4. A virus detection method comprising:
    diffusing a gas into an aqueous solution containing a fluorescent antibody specific for a virus, by bringing the gas into contact with the aqueous solution so that the fluorescent antibody binds to the virus in the gas;
    atomizing the aqueous solution and generating a mist of the aqueous solution in which the gas is diffused;
    measuring a fluorescence intensity of the mist; and
    comparing the measured fluorescence intensity with the fluorescence intensity of a mist without viruses,
    wherein the presence of a virus in the gas can be detected automatically on a real time basis if the measured fluorescence intensity is greater than the fluorescence intensity of a mist without viruses.

5. The virus detection method of claim 4, further comprising:
    introducing the aqueous solution and the gas into the liquid flow path and the gas flow path, respectively; and
    guiding the aqueous solution separated at the branch part into the atomization unit after the fluorescent antibody binds to the virus in the gas,
    wherein the gas diffusion into the aqueous solution and binding of the fluorescent antibody to the virus in the gas are performed by a diffusion unit, wherein the diffusion unit comprises:
    a diffusion flow path including a liquid flow path through which the aqueous solution flows;
    a gas flow path, formed in parallel to the liquid flow path, through which the gas flows while bringing the gas into contact with the aqueous solution flowing through the liquid flow path; and
    a branch part that is formed at an outlet of the diffusion flow path and configured to separate and discharge the gas and the aqueous solution.

* * * * *